(12) United States Patent
Harmon et al.

(10) Patent No.: US 9,486,540 B2
(45) Date of Patent: Nov. 8, 2016

(54) METHODS FOR DELIVERY TO THE CENTRAL NERVOUS SYSTEM OF NUCLEIC ACID NANOPARTICLES TO TREAT CENTRAL NERVOUS SYSTEM DISORDERS

(71) Applicants: Northeastern University, Boston, MA (US); Copernicus Therapeutics, Inc., Cleveland, OH (US)

(72) Inventors: Brendan Harmon, Patchogue, NY (US); Barbara Lee Waszczak, Wellesley, MA (US); Mark Cooper, Cleveland, OH (US)

(73) Assignees: Northeastern University, Boston, MA (US); Copernicus Therapeutics, Inc., Cleveland, OH (US)

( * ) Notice: Subject to any disclaimer, the term of this patent is extended or adjusted under 35 U.S.C. 154(b) by 0 days.

(21) Appl. No.: 14/383,311

(22) PCT Filed: Mar. 11, 2013

(86) PCT No.: PCT/US2013/030264
§ 371 (c)(1),
(2) Date: Sep. 5, 2014

(87) PCT Pub. No.: WO2013/134777
PCT Pub. Date: Sep. 12, 2013

(65) Prior Publication Data
US 2015/0111946 A1    Apr. 23, 2015

Related U.S. Application Data

(60) Provisional application No. 61/768,895, filed on Feb. 25, 2013, provisional application No. 61/725,662, filed on Nov. 13, 2012, provisional application No. 61/609,042, filed on Mar. 9, 2012.

(51) Int. Cl.
| | | |
|---|---|---|
| *A61K 48/00* | (2006.01) | |
| *C07H 21/02* | (2006.01) | |
| *C07H 21/04* | (2006.01) | |
| *C07K 14/475* | (2006.01) | |
| *C12N 15/87* | (2006.01) | |
| *A61K 9/00* | (2006.01) | |
| *A61K 9/51* | (2006.01) | |
| *A61K 47/48* | (2006.01) | |
| *C07K 14/47* | (2006.01) | |
| *C12N 15/113* | (2010.01) | |

(52) U.S. Cl.
CPC ......... *A61K 48/0041* (2013.01); *A61K 9/0043* (2013.01); *A61K 9/51* (2013.01); *A61K 47/48215* (2013.01); *A61K 48/0075* (2013.01); *C07K 14/475* (2013.01); *C07K 14/4705* (2013.01); *C12N 15/113* (2013.01); *C12N 15/87* (2013.01); *C12N 2310/11* (2013.01); *C12N 2310/351* (2013.01); *C12N 2830/008* (2013.01); *C12N 2999/007* (2013.01)

(58) Field of Classification Search
CPC . C12N 2310/11; C12N 15/113; A61K 48/00
See application file for complete search history.

(56) References Cited

U.S. PATENT DOCUMENTS

| | | | |
|---|---|---|---|
| 5,624,898 | A | 4/1997 | Frey, II |
| 5,844,107 | A | 12/1998 | Hanson et al. |
| 5,877,302 | A | 3/1999 | Hanson et al. |
| 5,972,900 | A | 10/1999 | Ferkol, Jr. et al. |
| 5,972,901 | A | 10/1999 | Ferkol, Jr. et al. |
| 6,008,336 | A | 12/1999 | Hanson et al. |
| 6,077,835 | A | 6/2000 | Hanson et al. |
| 6,180,603 | B1 | 1/2001 | Frey, II |
| 6,200,801 | B1 | 3/2001 | Ferkol, Jr. et al. |
| 6,281,005 | B1 | 8/2001 | Casal et al. |
| 6,313,093 | B1 | 11/2001 | Frey, II |
| 6,342,478 | B1 | 1/2002 | Frey, II |
| 6,407,061 | B1 | 6/2002 | Frey, II |
| 6,506,890 | B1 | 1/2003 | Cooper et al. |
| 6,991,785 | B2 | 1/2006 | Frey, II |
| 7,273,618 | B2 | 9/2007 | Frey, II et al. |
| 7,618,615 | B2 | 11/2009 | Frey, II et al. |
| 8,017,577 | B2 | 9/2011 | Cooper et al. |

FOREIGN PATENT DOCUMENTS

| | | |
|---|---|---|
| WO | WO-03/087323 A2 | 10/2003 |
| WO | WO-2005/023861 A2 | 3/2005 |
| WO | WO-2006/023286 A2 | 3/2006 |
| WO | WO-2007/016501 A2 | 2/2007 |

(Continued)

OTHER PUBLICATIONS

Bjorklund, A. et al., "Towards a neuroprotective gene therapy for Parkinson's disease: use of adenovirus, AAV and lentivirus vectors for gene transfer of GDNF to the nigrostriatal system in the rat Parkinson model," Brain Research, vol. 886, pp. 82-98 (2000).

Chen, X. et al., "Cell Surface Nucleolin Serves as Receptor for DNA Nanoparticles Composed of Pegylated Polysine and DNA," Molecular Therapy, vol. 16, No. 2, pp. 333-342 (Feb. 2008).

Chen, X. et al., "Nucleolin-Mediated Cellular Trafficking of DNA Nanoparticle Is Lipid Raft and Microtubule Dependent and Can Be Modulated by Glucocorticoid," Molecular Therapy, vol. 19, No. 1, pp. 93-102 (Jan. 2011).

Evers, M. M. et al., "Targeting Several CAG Expansion Diseases by a Single Antisense Oligonucleotide," PLoS ONE, vol. 6, No. 9, e24308, pp. 1-11 (Sep. 2011).

(Continued)

*Primary Examiner* — Amy Bowman
(74) *Attorney, Agent, or Firm* — Hamilton, Brook, Smith & Reynolds, P.C.

(57) ABSTRACT

Disclosed herein are methods and compositions for the treatment of diseases of the CNS with nucleic acid nanoparticles. Compositions are also disclosed herein that utilize nucleic acid nanoparticles to treat conditions such as Parkinson's Disease. Furthermore, methods of intranasally administering the compacted nucleic acid nanoparticles for therapeutic purposes in the brain are disclosed.

9 Claims, 17 Drawing Sheets

(56) References Cited

FOREIGN PATENT DOCUMENTS

| WO | WO-2008/147438 A2 | 12/2008 |
|---|---|---|
| WO | WO-2010/088927 A1 | 8/2010 |
| WO | WO-2011/088456 A2 | 7/2011 |

OTHER PUBLICATIONS

Fink, T. L. et al., "Plasmid size up to 20 kbp does not limit effective in vivo lung gene transfer using compacted DNA nanoparticles," Gene Therapy, vol. 13, pp. 1048-1051 (2006).

Fletcher, A. M. et al., "Transgene expression in the striatum following intracerebral injections of DNA nanoparticles encoding for human glial cell line-derived neurotrophic factor (hGDNF)," Neuroscience, vol. 194, pp. 220-226, 16 pages (Oct. 27, 2011).

Gill, S. S. et al., "Direct brain infusion of glial cell line-derived neurotrophic factor in Parkinson disease," Nature Medicine, vol. 9, pp. 589-595 (2003).

Griesenbach, U. et al., "Gene therapy for cystic fibrosis: an example for lung gene therapy," Gene Therapy, vol. 11, pp. S43-S50 (2004).

Hurelbrink, C. B. and Barker, R. A., "The potential of GDNF as a treatment for Parkinson's disease," Exp. Neurol., vol. 185, No. 1, pp. 1-6 (Jan. 2004).

International Search Report and Written Opinion issued by the U. S. Patent and Trademark Office as International Searching Authority for International Application No. PCT/US2013/030264 dated Jun. 19, 2013 (16 pages).

Konstan, M. W. et al., "Compacted DNA Nanoparticles Administered to the Nasal Mucosa of Cystic Fibrosis Subjects Are Safe and Demonstrate Partial to Complete Cystic Fibrosis Transmembrane Regulator Reconstitution," Human Gene Therapy, vol. 15, pp. 1-15 (Dec. 2004).

Lang, A. E. et al., "Randomized Controlled Trial of Intraputamenal Glial Cell Line-Derived Neurotrophic Factor Infusion in Parkinson Disease," Ann. Neurol., vol. 59, pp. 459-466 (2006).

LeWitt, P. A. and Taylor, D. C., "Protection against Parkinson's disease progression: clinical experience," Neurotherapeutics, vol. 5, No. 2, pp. 210-225 (Apr. 2008).

Liu, G. et al., "Nanoparticles of Compacted DNA Transfect Postmitotic Cells," J. Biol. Chem., vol. 278, No. 35, pp. 32578-32586 (Aug. 29, 2003).

Marks Jr., W. J. et al., "Gene delivery of AAV2-neurturin for Parkinson's disease: a double-blind, randomised, controlled trial," The Lancet Neurology, vol. 9, No. 12, pp. 1164-1172 (Dec. 2010).

McBride, J. L. et al., "Preclinical Safety of RNAi-Mediated HTT Suppression in the Rhesus Macaque as a Potential Therapy for Huntington's Disease," Molecular Therapy, vol. 19, No. 12, pp. 2152-2162 (Dec. 2011).

Sun, W. and Ziady, A. G., "Real-time imaging of gene delivery and expression with DNA nanoparticle technologies,"Methods Mol. Biol., vol. 544, pp. 525-546 (2009).

Wen et al., "Odorranalectin-conjugated nanoparticles: Preparation, brain delivery and pharmacodynamic study on Parkinson's disease following intranasal administration," Journal of Controlled Release, vol. 151, pp. 131-138 (Feb. 26, 2011).

Yurek, et al., "Compacted DNA Nanoparticle Gene Transfer of GDNF to the Rat Striatum Enhances the Survival of Grafted Fetal Dopamine Neurons," Cell Transplantation, vol. 18, No. 10, pp. 1183-1196, 22 pages (Jun. 22, 2009).

Yurek, et al., "Long-term Transgene Expression in the Central Nervous System Using DNA Nanoparticles," Molecular Therapy, vol. 17, No. 4, pp. 641-650 (Apr. 2009).

Ziady, A. G. et al., "Transfection of airway epithelium by stable PEGylated poly-L-lysine DNA nanoparticles in vivo," Mol. Ther., vol. 8, No. 6, pp. 936-947 (Dec. 2003).

Huang, et al., "Gene Therapy Using Lactoferrin-modified Nanoparticles in a Rotenone-induced Chronic Parkinson Model," Journal of Neurological Sciences, vol. 290, No. 1-2, pp. 123-130 (Mar. 15, 2010).

Huang, et al., "Neuroprotection in a 6-hydroxydopamine-lesioned Parkinson Model Using Lactoferrin-modified Nanoparticles," Journal of Gene Medicine, vol. 11, No. 9, pp. 754-763 (Sep. 1, 2009).

Partial Supplementary European Search Report issued by the European Patent Office for Application No. 13757391.1 dated Oct. 21, 2015 (9 pages).

Yang, H., "Nanoparticle-Mediated Brain-Specific Drug Delivery, Imaging, and Diagnosis," Pharmaceutical Research, vol. 27, No. 9, pp. 1759-1771 (Jul. 1, 2010).

Dhuria, et al., "Intranasal Delivery to the Central Nervous System: Mechanisms and Experimental Considerations," J. Pharmaceutical Sciences, vol. 99, No. 4, pp. 1654-1673 (Apr. 2010).

Extended European Search Report issued by the European Patent Office for European Patent Application No. 13757391.1 dated Mar. 9, 2016 (18 pgs.).

Harmon, et al., "Intranasal Administration of Plasmid DNA Nanoparticles Yields Successful Transfection and Expression of a Reporter Protein in Rat Brain," Gene Therapy, vol. 21, pp. 514-521 (2014).

Danielyan, et al., "Therapeutic Efficacy of Intranasally Delivered Mesenchymal Stem Cells in a Rat Model of Parkinson Disease," Rejuvenation Research, vol. 14, No. 1, pp. 3-16 (2011).

Van Velthoven, et al., "Nasal Administration of Stem Cells: A Promising Novel Route to Treat Neonatal Ischemic Brain Damage," Pediatric Research, vol. 68, No. 5, pp. 419-422 (2010).

Danielyan, et al., "Intranasal Delivery of Cells to the Brain," European Journal of Cell Biology, vol. 88, pp. 315-324 (2009).

Fransson, et al., "CAR/FoxP3-engineered T Regulatory Cells Target the CNS and Suppress EAE Upon Intranasal Delivery," Journal of Neuroinflammation, vol. 9, 12 pgs. (2012).

Conley, S. M. and Naash, M. I., "Nanoparticles for Retinal Gene Therapy," Prog Retin Eye Res., vol. 29(5), pp. 376-397 (Sep. 2010).

Glavaski-Joksimovic, et al., "Glial Cell Line-derived Neurotrophic Factor-secreting Genetically Modified Human Bone Marrow-derived Mesenchymal Stem Cells Promote Recovery in a Rat model of Parkinson's Disease," J Neurosci Res., vol. 88(12), pp. 2669-2681 (2010).

Read, et al., "POD Nanoparticles Expressing GDNF Provide Structural and Functional Rescue of Light-induced Retinal Degeneration in an Adult Mouse," Mol Ther., vol. 18(11), pp. 1917-1926 (2010).

Domb, Abraham J., and Neeraj Kumar, eds. *Biodegradable Polymers in Clinical Use and Clinical Development*, John Wiley & Sons, Ch. 15, 48 total pgs. (2011).

```
LOCUS       pGDNF_1b.seq            4064 bp    DNA     circular     07-MAR-2013
Plasmid name: pGDNF_1b
FEATURES             Location/Qualifiers
     misc_feature    8..414
                     /note="beta-Glo MAR"
     misc_feature    2505..2530
                     /note="SV40 pA"
     misc_feature    2536..3335
                     /note="IFN-beta S/MAR"
     misc_feature    3352..3417
                     /note="EM2K promoter"
     misc_feature    3418..3792
                     /note="Zeo R"
     misc_feature    3805..4064
                     /note="R6K ori"
     promoter        427..760
                     /vntifkey=Ubiquitin C promoter
                     /label=Ubiquitin C promoter
                     /note="Ubiquitin C promoter"
     exon            761..824
                     /vntifkey=UbC Exon I
                     /label=UbC Exon I
                     /note="UbC Exon I"
     intron          825..1636
                     /vntifkey=UbC intron 1
                     /label=Intron\1
                     /note="Intron 1"
     misc_feature    823..826
                     /note="SD"
     misc_feature    1635..1636
                     /note="SA"
     proprotein      1709..2284
```

FIG. 11A

```
                    /gene="GDNF"
                    /product="glial cell line derived neurotrophic factor
                    isoform 1 preprotein"
     mat_peptide    1883..2284
                    /gene="GDNF"
                    /product="glial cell line derived neurotrophic factor
                    isoform 1"
     misc_feature   1725..1802
                    /note="Sequence absent in variant-2"
     gene           1652..2297
                    /note="hGDNF-1b"
BASE COUNT     1156 a    789 c    1023 g    1096 t
ORIGIN
       1 TTAATTAAAA TTATCTCTAA CGCATCTGAA CTGCCTCTCT TCCTTTTCAT CTCTACTTCA
      61 TCTGCTACCT CTGTGACCTG AAACATATTT ATAATTCCAT TAAGCTGTGC ATATGATAGA
     121 TTTATCATAT GTATTTTCCT TAAAGGATTT TTGTAAGAAC TAATTGAATT GATACCTGTA
     181 AAGTCTTTAT CACACTACCC AATAAATAAT AAATCTCTTT GTTCAGCTCT CTGTTTCTAT
     241 AAATATGTAC CAGTTTTATT GTTTTTAGTG GTAGTGATTT TATTCTCTTT CTATATATAT
     301 ACACACACAT GTGTGCATTC ATAAATATAT ACAATTTTTA TGAATAAAAA ATTATTAGCA
     361 ATCAATATTG AAAACCACTG ATTTTTGTTT ATGTGAGCAA ACAGCAGATT AAAAGGAATT
     421 CCTGCAggcc tccgcgcagg gttttggcgc ctccgcggg cgccccctc ctcacggtga
     481 gcgctgccac gtcagacgaa gggcgcagcg agcgtcctga tccttccgcc ggacgctca
     541 ggacagcggc ccgctgctca taagactcgg ccttagaacc ccagtatcag cagaaggaca
     601 ttttaggacg ggacttgggt gactctaggg cactggtttt cttccagag agggaacag
     661 gcgaggaaaa gtagtccctt ctcggcgatt ctgcggaggg atctccgtcg gcggtgaac
     721 gtcgatgatt atataaggac gcgccggtg tggcacagct agttccgtcg cagctgggat
     781 ttgggtcgcg gtccttgttt gtggatcgct gtgatcgtca cctgctgagt agcgggctgc
     841 tgggctggcc ggggcttttcg tcgccgcggg gccgctcggt gggacggaag cgtgtggaga
     901 gaccgccaag ggctgtagtc tgggtccgcg agcaaggttg ccctgaactg cgggttgggg
     961 ggagcgcagc aaaatggcgg ctgttcccga gtcttgaatg gaagacgctt gtgaggcggg
    1021 ctgtgaggtc gttgaaacaa ggtgggggc atggtgggcg gcaagaaccc aaggtcttga
    1081 ggccttcgct aatgcgggaa agctcttatt cgggtgagat gggctgtggc accatctggg
```

FIG. 11B

```
1141 gaccctgacg tgaagtttgt cactgactgg agaactcggt ttgtcgtctg ttgcgagggc
1201 ggcagttatg gcggtgcgt tggcagtgc accgtacct ttggagcgc gcgccctcgt
1261 cgtgtcgtga cgtcaccgt tctgttggct tataatgcag ggtgggcca cctgcggta
1321 ggtgtgcggt aggcttttct ccgtgcagg acgcagggtt cgggcctagg gtaggctctc
1381 ctgaatcgac aggcgccgga cctctggtga ggggagggat aagtgaggcg tcagtttctt
1441 tggtcggttt tatgtaccta tcttcttaag tagctgaagc tcggttttty aactatgcgc
1501 tcggggttgg cgagtgtctt ttgtgaagtt ttttaggcac cttttgaaat gtaatcattt
1561 gggtcaatat gtaattttca gtgttagact agtaaattgt ccgctaaatt ctggccgttt
1621 ttggcttttt tgttagacga gctagcccac catgaagtta tgggatgtcg tggctgtctg
1681 cctggtgctg ctccacaccg cgtccgcctt ccgctgccc gcggCaaga ggctcccga
1741 gggcccgcc gaagaccgct cctcggccg ccgccgcgcg ccttcgcgc tgagcagtga
1801 ctcaaatatg ccagaggatt atcctgatca gttcgatgat gtcatggatt ttattcaagc
1861 caccattaaa agactgaaaa ggtcaccaga taaacaaatg gcagtgcttc ctagaagaga
1921 gcggaatcgg caggctgcag ctgccaaccc agagaattcc agaggaaaag gtcggagcg
1981 ccagggggc aaaaaccggg gtgtgtctt aactgcaata catttaaatg tcactgactt
2041 gggtctgggc tatgaaacca aggaggaact gattttagg tactgcagcg gctcttgcga
2101 tgcagctgag acaacgtacg acaaaatatt gaaaaactta tctagaaata gaaggctggt
2161 gagtgacaaa gtagggcagg catgttgcag accatcgcc tttgatgatg acctgtcgtt
2221 tttagatgat acctggttt accatattct aagaaagcat tccgctaaaa ggtgtggatg
2281 tatctgataa tctagactag CTGGCCAGAC ATGATAAGAT ACATTGATGA GTTTGGACAA
2341 ACCACAACTA CAATCCACTC AAAAAAATCC TTTATTTCTC AAATTTCTCA TCCTATTCCT
2401 TTATTTGTAA CCATTATAAG CTGCAATAAA CAAGTTAACA ACAACAATTG CATTCATTTT
2461 ATGTTTCAGG TTCAGGGGGA GGTGTGGGAG GTTTTTTAAA GCAAGTAAAA CCTCTACAAA
2521 TGTGGTATGG AATTCAGTCA ATATGTTCAC CCCAAAAAAG CTGTTTGTTA ACTTGCCAAC
2581 CTCATTCTAA AATGTATATA GAAGCCCAAA AGACAATAAC AAAAATATTC TTGTAGAACA
2641 AAATGGGAAA GAATGTTCCA CTAAATATCA AGATTTAGAG CAAAGCATGA GATGTGTGGG
2701 GATAGACAGT GAGGCTGATA AAATAGAGTA GAGCTCAGAA ACAGACCCAT TGATATATGT
2761 AAGTGACCTA TGAAAAAAAT ATGGCATTTT ACAATGGCAA AATGATGATC TTTTTCTTTT
2821 TTACAAAAAC ACGCAAATAT ATTTATATCT AAAAAATAAA ACGGAACCCA TATGTCATAC
2881 CATACACACA AAAAAATTCC AGTGAATTAT AAGTCTAAAT GGAGAAGGCA AAACTTTAAA
2941 TCTTTTAGAA AATAATATAG AAGCATGCCA TCAAGACTTC AGTGTAGAGA AAAATTTCTT
3001 ATGACTCAAA GTCCTAACCA CAAAGAAAAG ATTGTTAATT AGATTGCATG AATATTAAGA
```

FIG. 11C

```
3061 CTTATTTTTA AAATAAAAA ACCATTAAGA AAAGTCAGGC CATAGAATGA CAGAAAATAT
3121 TTGCAACACC CCAGTAAAGA GAATTGTAAT ATGCAGATTA TAAAAGAAG TTTACAAAT
3181 CAGTAAAAAA TAAAACTAGA CAAAAATTTG AACAGATGAA AGAGAAACTC TAAATAATCA
3241 TTACACATGA GAAACTCAAT CTCACAAATC AGACAACTAT CATTGCATAT ACACTAAATT
3301 ACAGAAATAT TAAAACCCTA AGTAACATCT CTTCCTTAAT TAAAACAGTA GTTCACAATT
3361 AAACATTGGC ATAGTATATC TGCATAGTAT AATACAACTC ACTATAGGAG GGCCATCATG
3421 GCCAAGTTCA CCAGTGCTGT CCCAGTGCTC ACAGCCAGGG ATGTGCCTGG AGCTCTTGAG
3481 TTCTGGACTG ACAGGTTGGG GTTCTCCAGA GATTTGTGG AGGATGACTT TGCAGGTGTG
3541 GTCAGAGATG ATGTCACCCT GTTCATCTCA GCAGTCCAGG ACCAGGTGGT GCCTGACAAC
3601 ACCCTGGCTT GGGTGTGGGT GAGAGGACTG GATGAGCTGT ATGCTGAGTG GAGTGAGGTG
3661 GTCTCCACCA ACTTCAGGGA TGCCAGTGGC CCTGCCATGA CAGAGATTGG AGAGCAGCCC
3721 TGGGGAGAG AGTTTGCCCT GAGAGACCCA GCAGGCAACT GTGTGCACTT TGTGGCAGAG
3781 GAGCAGGACT GAGGATAACC TAGGAAACCT TAAAACCTTT AAAAGCCTTA TATATTCTTT
3841 TTTTTCTTAT AAAACTTAAA ACCTTAGAGG CTATTTAAGT TGCTGATTTA TATTAATTTT
3901 ATTGTTCAAA CATGAGAGCT TAGTACATGA AACATGAGAG CTTAGTACAT TAGCCATGAG
3961 AGCTTAGTAC ATTAGCCATG AGGGTTTACT TCATTAAACA TGAGAGCTTA GTACATTAAA
4021 CATGAGAGCT TAGTACATAC TATCAACACG TTGAACTGCT GATC
```

```
LOCUS      GDNF1-b precursor amino acid sequence       211 aa    PRO
Thu, Mar 07, 2013

Translate DNA Sequence GDNF1-b precursor coding sequence.seq(1,633)
With Standard Genetic Code Molecular Weight 23720.21 Daltons 211 Amino Acids 36 Strongly Basic(+) Amino Acids (K,R)

27 Strongly Acidic(-) Amino Acids (D,E)

68 Hydrophobic Amino Acids (A,I,L,F,W,V)

48 Polar Amino Acids (N,C,Q,S,T,Y)

9.065 Isoelectric Point 9.346 Charge at PH 7.0

Total number of bases translated is 633
       % A = 26.70              [169]

% G = 27.01              [171]

% T = 22.12              [140]

% C = 24.17              [153]

% Ambiguous =  0.00      [0]

% A+T = 48.82            [309]

% C+G = 51.18            [324]

BASE COUNT      169 a    153 c    171 g    140 t

Davis,Botstein,Roth Melting Temp C. 65.10
       Wallace Temp C                      2220.00
Codon usage:
gca  Ala(A)    5  # cag  Gln(Q)    4  # uug  Leu(L)    2  # uaa  Ter(.)    0
gcc  Ala(A)    6  # ---  Gln(Q)    6  # ---  Leu(L)   21  # uag  Ter(.)    0
```

FIG. 12A

| | | | | | | | | | | | |
|---|---|---|---|---|---|---|---|---|---|---|---|
| gcg | Ala(A) | 4 | # | gaa | Glu(E) | 3 | # | aaa | Lys(K) | 9 | # | uga | Ter(.) | 0 |
| gcu | Ala(A) | 5 | # | gag | Glu(E) | 6 | # | aag | Lys(K) | 4 | # | --- | Ter(.) | 0 |
| --- | Ala(A) | 20 | # | --- | Glu(E) | 9 | # | --- | Lys(K) | 13 | # | aca | Thr(T) | 1 |
| aga | Arg(R) | 9 | # | gga | Gly(G) | 2 | # | aug | Met(M) | 4 | # | acc | Thr(T) | 3 |
| agg | Arg(R) | 6 | # | ggc | Gly(G) | 6 | # | --- | Met(M) | 4 | # | acg | Thr(T) | 1 |
| cga | Arg(R) | 0 | # | ggg | Gly(G) | 1 | # | uuc | Phe(F) | 3 | # | acu | Thr(T) | 2 |
| cgc | Arg(R) | 4 | # | ggu | Gly(G) | 3 | # | uuu | Phe(F) | 4 | # | --- | Thr(T) | 7 |
| cgg | Arg(R) | 4 | # | --- | Gly(G) | 12 | # | --- | Phe(F) | 7 | # | ugg | Trp(W) | 1 |
| cgu | Arg(R) | 0 | # | cac | His(H) | 1 | # | cca | Pro(P) | 3 | # | --- | Trp(W) | 1 |
| --- | Arg(R) | 23 | # | cau | His(H) | 3 | # | ccc | Pro(P) | 5 | # | uac | Tyr(Y) | 3 |
| aac | Asn(N) | 4 | # | --- | His(H) | 4 | # | ccg | Pro(P) | 1 | # | uau | Tyr(Y) | 2 |
| aau | Asn(N) | 5 | # | aua | Ile(I) | 2 | # | ccu | Pro(P) | 3 | # | --- | Tyr(Y) | 5 |
| --- | Asn(N) | 9 | # | auc | Ile(I) | 2 | # | --- | Pro(P) | 12 | # | gua | Val(V) | 1 |
| gac | Asp(D) | 6 | # | auu | Ile(I) | 4 | # | agc | Ser(S) | 2 | # | guc | Val(V) | 5 |
| gau | Asp(D) | 12 | # | --- | Ile(I) | 8 | # | agu | Ser(S) | 2 | # | gug | Val(V) | 4 |
| --- | Asp(D) | 18 | # | cua | Leu(L) | 1 | # | uca | Ser(S) | 2 | # | guu | Val(V) | 1 |
| ugc | Cys(C) | 4 | # | cuc | Leu(L) | 2 | # | ucc | Ser(S) | 5 | # | --- | Val(V) | 11 |
| ugu | Cys(C) | 4 | # | cug | Leu(L) | 10 | # | ucg | Ser(S) | 1 | # | nnn | ???(X) | 0 |
| --- | Cys(C) | 8 | # | cuu | Leu(L) | 1 | # | ucu | Ser(S) | 1 | # | TOTAL | | 211 |
| caa | Gln(Q) | 2 | # | uua | Leu(L) | 5 | # | --- | Ser(S) | 13 | # | | | |

```
...
ORIGIN
        1 MKLWDVVAVC LVLLHTASAF PLPAGKRPFE APAEDRSLGR RRAPFALSSD SNMPEDYPDQ
       61 FDDVMDFIQA TIKRLKRSPD KQMAVLPRRE RNEQAAAANP ENSRGKGRRG QRGKNRGCVL
      121 TAIHLNVTDL GLGYETKEEL IFRYCSGSCD AAETTYDKIL KNLSRNRRLV SDKVGQACCR
      181 PIAFDDDLSF LDDNLVYHIL RKHSAKRCGC I
//
```

FIG. 12B

METHODS FOR DELIVERY TO THE CENTRAL NERVOUS SYSTEM OF NUCLEIC ACID NANOPARTICLES TO TREAT CENTRAL NERVOUS SYSTEM DISORDERS

CROSS REFERENCE TO RELATED APPLICATIONS

This application is a national stage application of International Application No. PCT/US13/30264, filed on Mar. 11, 2013, incorporated herein by reference in its entirety, which claims priority under 35 U.S.C. §119(e) to U.S. Provisional Application No. 61/768,895, filed on Feb. 25, 2013, 61/725,662, filed on Nov. 13, 2012, and 61/609,042, filed on Mar. 9, 2012, incorporated herein by reference in their entirety.

FIELD OF THE INVENTION

The present invention relates to the field of medicine. More specifically, the present invention relates to gene therapy and delivery of such therapeutics to the central nervous system to treat or prevent diseases of the central nervous system.

BACKGROUND

The treatment of most central nervous system ("CNS") diseases faces two issues: (1) developing therapeutics that treat the actual cause of the disease and (2) getting therapeutic agents to the CNS across the blood brain barrier ("BBB"). Regarding the first issue, most agents seek to ameliorate the effects of the particular disease rather than treat the actual cause of the condition, which may be the loss or abnormal activity of particular neurons necessary for normal brain function. For instance, the available drugs on the market for Parkinson's Disease mimic or replace the lost dopamine, but do not get to the heart of the problem, which is the progressive loss of the dopamine neurons (see, e.g., LeWitt and Taylor, (2008) *Neurotherapeutics*. 5:210-225). As such, therapies that protect against loss of neuronal populations would be an advance over present therapies that are available for many diseases.

One potential therapy is gene therapy. Gene therapy has been shown to be effective to treat certain diseases by allowing abnormal cells to function normally. Such therapy can be gene replacement, wherein a normal copy of the disease-causing gene is introduced into affected cells. Such disease-causing genes are typically aberrant due to gene mutation, but levels of gene expression due to mutations in gene expression control regions, or in transcription factors, may result in the pathogenesis of disease. Alternatively, gene therapy can introduce a nucleic acid that expresses a therapeutic protein which improves the survival or function of cells that are vulnerable to a disease process without correcting the underlying cause of the disease. Such disease-modifying nucleic acids are not gene replacement. And gene therapy also can introduce or express an anti-sense moiety, thereby reducing levels of disease-inducing RNAs and proteins. An example of gene replacement therapy is the treatment of cystic fibrosis by providing the cystic fibrosis transmembrane conductance regulator (CFTR) gene to lung cells that do not have a normal copy of this gene (see Griesenbach et al. (2004) *Gene Therapy* 11: S43-S50; Konstan M W, Davis P B, Wagener J S, Hilliard K A, Stern R C, Milgram L J H, Kowalczyk T H, Hyatt S L, Fink T L, Gedeon C R, Oette S M, Payne J M, Muhammad O, Ziady A G, Moen R C, and Cooper M J. (2004) *Human Gene Ther,* 15:1255-1269.). An example of gene therapy to improve survival of vulnerable or damaged cells is the treatment of Parkinson's disease with a gene for a neurotrophic factor (see Bjorklund et al., (2000) *Brain Res.* 886: 82-98; Hurelbrink and Barker, (2004) *Exp. Neurol.* 185: 1-6.). Nevertheless, these therapies have faced the hurdle to get the gene therapy to the proper cells, and to get the cells to produce the therapeutic protein at appropriate levels, even without the BBB acting as a barrier to getting therapeutics to the proper cells (id.).

Regarding the issue of the BBB, one technique employed in the prior art has been intracranial injection of therapeutics into the brain. For example, glial cell line-derived neurotrophic factor ("GDNF") protein has been injected into the brains of Parkinson's disease patients (see, e.g., Gill et al. (2003) *Nature Med.* 9: 589-595; Lang, et al. (2006) *Ann. Neurol.* 59: 459-466.). Similarly, the gene for neurturin, a GDNF analog, has also been injected into the brains of Parkinson's patients (see, e.g. Marks Jr et al. (2010) *Lancet Neurology* 9: 1164-1172). As for most gene therapies, the neuturin gene was inserted into a viral vector that helps get it into cells. The technique of intracerebral injection and the use of viral vectors pose safety risks such as potential damage to brain tissue, hemorrhage, immunogenic reactions to the viral vector, and issues relating to infection and the inherent trauma associated with brain surgery. Furthermore, such injections often treat only the cells within a few millimeters of the injection track. To treat a wider area requires multiple injection tracks which increase the likelihood of certain safety risks such as hemorrhage and potential damage to brain tissue. If the disease requires treatment of a large segment of the CNS, the risks of numerous injections are of concern; especially if one or more large areas involving multiple structures such as cerebellum, brainstem and cerebrum need to receive treatment.

Accordingly, there remains a need for methods and formulations that allow for the treatment of the causes of neurodegenerative diseases without necessitating direct injection (often multiple injection tracks are needed for even a small defined area of treatment) into the brain or the need for viral vectors. In addition, there remains a need for methods and formulations that allow for therapeutics to circumvent the BBB to safely and effectively get therapeutics to the CNS.

SUMMARY

The present disclosure provides methods and compositions for the delivery of gene sequences to the CNS. In particular, the disclosed methods and compositions allow for administration intranasally. The methods and compositions disclosed herein allow for improved transit and expression of gene therapies, such as a gene encoding for GDNF activity, across the BBB. In addition, the methods and compositions disclosed herein provide for improved treatment of diseases such as Parkinson's Disease.

Aspects disclosed herein relate to a method for delivering and expressing a nucleic acid sequence in the brain. The method comprises intranasal administration of nucleic acid nanoparticles, wherein the nanoparticles comprise a ratio of about one molecule of nucleic acid per one nanoparticle.

In certain embodiments, the nucleic acid sequence encodes a therapeutic protein. In other embodiments, the nucleic acid sequence encodes a therapeutic anti-sense moiety. In particular embodiments, the nucleic acid sequence comprises a therapeutic anti-sense moiety. In certain embodiments, the nucleic acid nanoparticle further comprises a polycation. In particular embodiments, the polycation is a polylysine.

In some embodiments, the nucleic acid nanoparticles comprise plasmid DNA. In particular embodiments, the nucleic acid sequence comprises a nucleic acid sequence of SEQ ID NO: 1. In more particular embodiments, the nucleic acid sequence encodes a polypeptide having GDNF activity. In still more particular embodiments, the polypeptide has an amino acid sequence of SEQ ID NO: 2.

In additional aspects, the disclosed methods relate to protecting neurons of a subject from cell death. The methods comprise intranasally administering an effective amount of therapeutic nucleic acid nanoparticles to the subject, wherein the nanoparticles express a product that protects the neurons from cell injury or promotes recovery from cell injury.

In certain embodiments, the product is a polypeptide. In particular embodiments, the polypeptide is a polypeptide that has GDNF activity. In further embodiments, the polypeptide has the amino acid sequence of SEQ ID NO: 2. In still further embodiments, the polypeptide is a polypeptide having an activity selected from the group consisting of neurturin, artemin, persephin, SDF-1, brain-derived neurotrophic factor (BDNF); activity dependent neurotrophic fact (ADNP), nerve growth factor (NGF); insulin, insulin-like growth factor-1 (IGF-1), oxytocin, neurotensin; cholecystokinin; neuropeptide Y; luteinizing-hormone-releasing hormone; growth hormone; arginine vasopressin; interferon; cytokines including IL-1, IL-2, IL-4, IL-6, IL-12, IL-17, TNF, and TGF; anti-VEGF polypeptides; peptides having anti-tumor activity; and scFv peptides that are able to modulate various biological functions by directly targeting components of the cells themselves or by interacting with various signaling mechanisms of both neural and non-neural cells, such as cytokines or autocrine factors.

In other embodiments, the neurons of the subject are dopaminergic neurons. In more embodiments, the neurons of the subject are located in the substantia nigra. In still more embodiments, the neurons of the subject are located in the hippocampus. In yet more embodiments, the neurons of the subject are located in the cerebral cortex, including the medial prefrontal cortex. In other embodiments, the neurons of the subject are motor neurons. There are many other neurotrophic factors known in the art and such factors are within the scope of the disclosed methods.

In certain embodiments, the nanoparticles further comprise a polycation. In particular embodiments, the polycation is polylysine. In more particular embodiments, the nanoparticle is a CK-PEG-GDNF nanoparticle.

In other embodiments, intranasally administering an effective amount of nanoparticles treats a subject suffering from Parkinson's Disease. In yet other embodiments, intranasally administering an effective amount of nanoparticles treats a subject suffering from a disease selected from the group consisting of Huntington Disease, Alzheimer's disease, dementia, Batten's disease, Tay Sach's disease, multiple sclerosis, depression, alcoholism, substance dependence, autism spectrum disorders, post-traumatic stress disorder (PTSD), traumatic brain injury (TBI), chronic traumatic encephalopathy (CTE), CNS lupus, autoimmune diseases of the CNS, epilepsy, stroke, amyotrophic lateral sclerosis, pain disorders, and neuromuscular diseases.

In certain embodiments, the effective amount of therapeutic nucleic acid nanoparticles is 0.1 ng to 1.0 ug. In some embodiments, the effective amount of therapeutic nucleic acid nanoparticles is 1.0 µg to 1 mg. In yet additional embodiments, the effective amount of therapeutic nucleic acid nanoparticles is 1.0 mg to 1 gm.

In particular embodiments, doses of therapeutic nucleic acid nanoparticles are administered intranasally as droplets, aerosolized as a spray mist, or using a pump for delivery for minutes to hours. In more particular embodiments, doses of therapeutic nucleic acid nanoparticles are administered intranasally multiple times over a defined time course. In even more particular embodiments, each CK-PEG-GDNF nanoparticle comprises a plasmid having a nucleic acid sequence of SEQ ID NO: 1. In even more particular embodiments, SEQ ID NO: 1 expresses a polypeptide with the amino acid sequence of SEQ ID NO: 2.

In some embodiments, the polypeptide protects the neuron from cell death. In certain embodiments, the product is an anti-sense RNA.

Further aspects disclosed herein relate to methods for treating a subject suffering from a brain or brainstem disorder. Such methods comprise administering intranasally an effective amount of compacted nucleic acid nanoparticles to the subject, wherein the population of nanoparticles comprises a ratio of about one molecule of nucleic acid per one nanoparticle, said nucleic acid encoding or comprising a therapeutic moiety. In certain embodiments, the nanoparticles treat the brain or brainstem disorder.

In particular embodiments, the nanoparticles comprise a nucleic acid encoding a product. In more particular embodiments, the product is a polypeptide.

In certain embodiments, the product is a polypeptide having an activity selected from the group consisting of GDNF, neurturin, persephin, artemin, SDF-1, brain-derived neurotrophic factor (BDNF), insulin, insulin-like growth factor-1 (IGF-1), nerve growth factor (NGF), activity-dependent neurotrophic factor (ADNP), insulin, insulin-like growth factor 1 (IGF-1), oxytocin, and beta-interferon, neurotensin, cholecystokinin, neuropeptide Y, luteinizing-hormone-releasing hormone, growth hormone, arginine vasopressin, interferon, cytokines including IL-1, IL-2, IL-4, IL-6, IL-12, IL-17, TNF, and TGF; anti-VEGF polypeptides; peptides having anti-tumor activity; and scFv peptides that are able to modulate various biological functions by directly targeting components of the cells themselves or by interacting with various signaling mechanisms of both neural and non-neural cells, such as cytokines or autocrine factors.

In some embodiments, the polypeptide has an amino acid sequence of SEQ ID NO: 2. In other embodiments, the product is an anti-sense RNA. In still other embodiments, the nanoparticle comprises an RNA molecule. In further embodiments, the nanoparticle comprises an mRNA molecule. In yet further embodiments, the nanoparticle comprises an anti-sense molecule.

In certain embodiments, the brain or brainstem disorder is selected from the group consisting of Parkinson's Disease, Huntington Disease, Alzheimer's disease, dementia, Batten's disease, Tay Sach's disease, multiple sclerosis, depression, alcoholism, substance dependence, autism spectrum disorders, post-traumatic stress disorder (PTSD), traumatic brain injury (TBI), chronic traumatic encephalopathy (CTE), CNS lupus, autoimmune diseases of the CNS, epilepsy, stroke, amyotrophic lateral sclerosis, pain disorders, and neuromuscular diseases.

In particular embodiments, the effective amount of therapeutic nucleic acid nanoparticles is 1.0 µg to 1 mg. In more particular embodiments, the effective amount of therapeutic nucleic acid nanoparticles is 1.0 mg to 1 gm. In even more particular embodiments, doses of therapeutic nucleic acid nanoparticles are administered intranasally as droplets, aerosolized as a spray mist, or using a pump for delivery for minutes to hours. In certain embodiments, doses of therapeutic nucleic acid nanoparticles are administered intranasally multiple times over a defined time course.

DESCRIPTION OF THE FIGURES

The following figures are presented for the purpose of illustration only, and are not intended to be limiting.

FIGS. 11A-11D show the sequence of pGDNF-1b (SEQ ID NO:1).

FIGS. 12A-12B show the amino acid sequence of GDNF-1b (SEQ ID NO:2).

DETAILED DESCRIPTION

Figure 1:
FIG. 1 shows the structure of the pGDNF-1b plasmid used in experiments on rats.

All publications, patent applications, patents, including GenBank database sequences, and other references mentioned herein are incorporated by reference in their entirety. In case of conflict, the present specification, including definitions, will control. In addition, the materials, methods, and examples are illustrative only and not intended to be limiting.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

1. Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The terms "glial cell line-derived neurotrophic factor" and "GDNF" as used in this disclosure refers to any polypeptide sequence or partial polypeptide sequence that exhibits glial cell line-derived neurotrophic factor activity. Furthermore, the terms include the nucleic acid sequence of the naturally occurring gene, which can include promoter and other control sequences, that encodes for polypeptide having glial cell line-derived neurotrophic factor activity. The terms include recombinant nucleic acid sequences and nucleic acid sequences generated by PCR that encode a polypeptide that exhibits glial cell line-derived neurotrophic factor activity.

The articles "a" and "an" are used in this disclosure to refer to one or more than one (i.e., to at least one) of the grammatical object of the article. By way of example, "an element" means one element or more than one element.

The term "or" is used in this disclosure to mean, and is used interchangeably with, the term "and/or," unless indicated otherwise.

The term "about" is used in this disclosure to mean a value − or +20% of a given numerical value. Thus, "about 60%" means a value between 60 minus 12% of 60 and 60 plus 12% of 60 (i.e., between 48% and 72%).

2. Methods of Administering Nanoparticles

The disclosure provides, in part, methods of protecting neurons of a subject from cell death. In certain embodiments disclosed herein, the methods comprise intranasally administering an effective amount of CK-PEG-GDNF nanoparticles to the subject. As used herein, a "CK-PEG-GDNF nanoparticle" is a plasmid DNA compacted into a nanoparticle comprising a polycationic peptide in which the plasmid carries a nucleic acid sequence that encodes a polypeptide having GDNF activity. In certain embodiments, the CK-PEG-GDNF nanoparticles further comprise polylysine peptides that include a cysteine residue and are conjugated with PEG. Intranasal administration of compacted plasmid DNA nanoparticles can be performed by a variety of means. For instance, the nanoparticles can be administered to the nasal cavity using a pump or other device which delivers a spray that aerosolizes the nanoparticles into a mist. Furthermore, the nanoparticles can be administered as droplets using a dropper or syringe or any device that disperses and applies the nanoparticles directly to the nasal mucosa.

Figure 10:
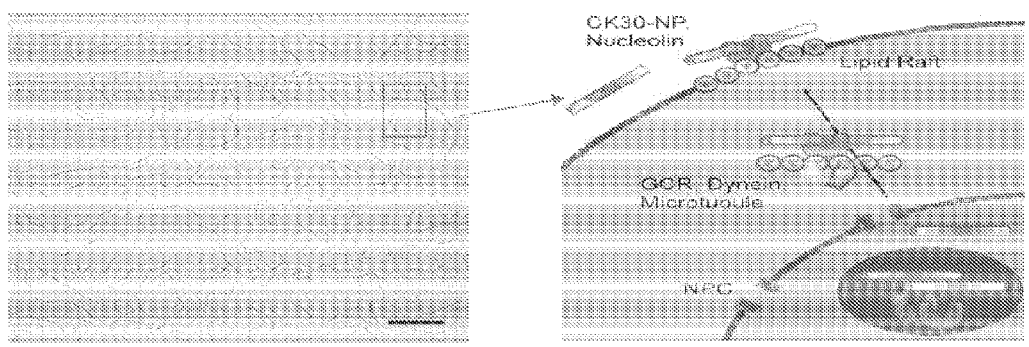
FIG. 10 shows an electron micrograph of PEGylated polylysine DNA nanoparticles (left) (Scale bar=200 nm). In addition, the theory behind how these nanoparticles enter the cell is shown (right).

Without being held to any particular theory, the nanoparticles disclosed herein can enter the cell by binding to nucleolin receptors on the cell surface (FIG. 10; see also Chen X, Kube D M, Cooper M J, and Davis P B. (2008) *Mol Ther.* 16(2):333-342; Chen X, Shank S, Davis P B, and Ziady A G. (2011) *Mol. Ther.* 19(1):93-102). Nanoparticles are internalized and transported to the nucleus via microtubules through the nuclear pore complex ("NPC") (id.). However, naked plasmid, not compacted into nanoparticles, does not bind to nucleolin and does not readily transfect cells. Thus, compacted nanoparticles can be a useful therapeutic delivery agent of a gene of interest. It is important to note, however, that other internalization and cellular trafficking pathways may be operative for nanoparticles applied to various tissues. The nucleolin-mediated internalization and trafficking pathway for DNA nanoparticles is best described for lung gene transfer, and the exact mechanism in CNS cells may be nucleolin-mediated or via other uptake and internalization pathways.

In certain embodiments disclosed herein, the nanoparticles are administered in an effective amount to provide a therapeutic effect to the subject. The amount of nanoparticles administered to the patient can be adjusted to take account of the subject's age, weight, and other factors, as needed to generate the desired amount of the protein produced by the gene in the desired location in the brain. For instance, in some embodiments, a subject is administered an effective amount of nanoparticles of about 0.01 ng of nanoparticles to about 100 ng of nanoparticles. In other embodiments, the subject is administered an effective amount of nucleic acid nanoparticles about 0.1 ng of nanoparticles to about 10 ng of nanoparticles. In particular embodiments, the effective amount of nucleic acid nanoparticles is about 100 ng of nanoparticles to about 1.0 µg of nanoparticles, about 1.0 µg of nanoparticles to about 100 µg of nanoparticles, or about 100 µg of nanoparticles to about 1.0 mg of nanoparticles. In certain instances, the effective amount of nucleic acid nanoparticles is about 1.0 mg of nanoparticles to about 10 mg of nanoparticles, about 10 mg of nanoparticles to about 100 mg of nanoparticles, and the effective amount of nucleic acid nanoparticles is about 100 mg of nanoparticles to 1.0 g of nanoparticles.

In further embodiments, the effective amount of nanoparticles is provided in a concentration of about 0.1 ng/ml to about 10 ng/ml, about 10 ng/ml to about 100 ng/ml, about 100 ng/ml to about 1.0 µg/ml, about 1.0 µg/ml to about 100 µg/ml, about 100 µg/ml to about 1.0 mg/ml, or about 1.0 mg/ml to about 10 mg/ml Aspects of the methods disclosed herein comprise providing a subject with an effective amount of nucleic acid nanoparticles in a liquid form. In particular embodiments, the nucleic acid nanoparticles comprise CK-PEG-GDNF nanoparticles. In certain embodiments, the effective amount of nanoparticles is provided in an aqueous solution. An example of an aqueous solution is pure water. In some embodiments, the aqueous solution is a saline solution. The sodium chloride can be provided in an amount that renders the solution isotonic with blood (e.g., about 300 mOs/L).

In more embodiments, a NaCl solution can be used in combination with dextrose or other sugars. In particular embodiments, the dextrose is in the solution at a concentration of 5% dextrose. In more particular embodiments, the saline solution comprises 39 mEq/L of Na and Cl and 5% dextrose. In other embodiments, a saline solution contains 77 mEq/L of Na and Cl and up to 50 g/L glucose.

Additional aqueous solutions are buffered solutions that maintain the pH of the solution between 6.5 and 7.5. An example of buffered solutions include Tris-buffered or phosphate-buffered saline, which is well known in the art.

The solutions can comprise agents that preserve the integrity of DNA in the nanoparticles by reducing nicking. Such agents include anti-oxidants and chelators, such as ethylene diamine tetraacetic acid (EDTA) or diethylene triamine pentaacetic acid (DTPA).

Aspects of the disclosed methods comprise administering nanoparticles of compacted plasmid DNA that contains at least one copy of a nucleic acid sequence that encodes a polypeptide having GDNF activity. In particular embodiments, the nucleic acid sequence is SEQ ID NO: 1. In other embodiments, the nucleic acid sequence is selected from the group consisting of GenBank Accession Nos. NM_001190468, NM_000514, NM_001190469, NM_199231, and NG_011675.

In certain embodiments, the nucleic acid sequence encodes a polypeptide having an amino acid sequence of SEQ ID NO: 2. In other embodiments, the nucleic acid sequence encodes a polypeptide having an amino acid sequence selected from the group consisting of Accession Nos. P39905, NP_000505, NP_001177397, NP_001177398, and NP_954701.

Aspects of the methods comprise administering CK-PEG-GDNF nanoparticles to a subject in which the plasmid DNA allows for expression of a polypeptide having GDNF activity. In certain embodiments, the nucleic acid has a sequence of SEQ ID NO: 1. Absolute sequence identity with any of the GDNF sequences disclosed herein is not required to obtain a therapeutic benefit from the CK-PEG-GDNF nanoparticles. For instance, the nucleic acid sequence encoding a polypeptide having GDNF activity can have 85% to 95% identity with a sequence selected from SEQ ID NO: 1. In other embodiments, the nucleic acid can have a 85% to 95% identity with a sequence selected from the group consisting of NM_001143805, NM_001143806, NM_001143808, NM_001143809, NM_001143810, NM_001143811, NM_001143812, NM_001143813, NM_001143814, NM_001143816, NM_001709, NM_170731, NM_170732, NM_170733, NM_170734, NM_001190468, NM_000514, NM_001190469, NM_199231, and NG_011675. This is due, in part, to the existence of "wobble" in nucleic acid sequences that code for amino acids, as is well-described in the art.

Aspects of the disclosed methods also allow for nucleic acid sequences that encode partial sequences of SEQ ID NO: 2. In addition, it should be recognized that deviations from the amino acid sequences of the polypeptide sequences disclosed herein is allowed. For instance, the amino acid sequence of the polypeptides can have 85% to 95% identity with the sequences disclosed herein.

3. Treatment of Diseases

Aspects of the disclosed methods relate to using therapeutic nanoparticles to treat neurological diseases. The methods comprise intranasally administering an effective amount of compacted nucleic acid nanoparticles to treat a subject suffering from a disease. In particular embodiments, compacted plasmid DNA nanoparticles transfect cells with the DNA encoding a polypeptide. The polypeptide can comprise a polypeptide having an activity necessary for normal cell function or health. For instance, the polypeptide can have GDNF activity. The polypeptide can replace or supplement endogenous GDNF activity in areas of the brain where the damaged or dying cells are located and by so doing, promote their recovery and restore their normal function. In certain embodiments, the polypeptide having GDNF activity protects neurons from cell death, thereby treating the disease. GDNF or other proteins also may be effective in recruiting neural stem cells into the brain.

In other embodiments, the nucleic acid nanoparticles supplement the activity of a gene product in damaged or dying cells. Examples of such gene products include GDNF, neurturin, persephin, artemin, brain-derived neurotrophic factor (BDNF), SDF-1, nerve growth factor (NGF), activity-dependent neurotrophic factor (ADNP), insulin, insulin-like growth factor 1 (IGF-1), oxytocin, and beta-interferon, neurotensin, cholecystokinin, neuropeptide Y, luteinizing-hormone-releasing hormone, growth hormone, arginine vasopressin, interferon, cytokines including IL-1, IL-2, IL-4, IL-6, IL-12, IL-17, TNF, and TGF, anti-VEGF polypeptides; peptides having anti-tumor activity; and scFv peptides that are able to modulate various biological functions by directly targeting components of the cells themselves or by interacting with various signaling mechanisms of both neural and non-neural cells, such as cytokines or autocrine factors.

In some aspects, the nucleic acid is RNA such as mRNA and anti-sense RNA. In some embodiments, a nucleic acid segment from a gene-of-interest expressed from a nanoparticle comprising a DNA, such as a plasmid DNA molecule, so that the antisense strand of RNA is transcribed. In other embodiments, the nanoparticle contains the anti-sense RNA itself. It is known in the art that such anti-sense RNA can repress gene function. For example, Huntington's Disease has been treated with anti-sense RNA technology (see, e.g., Evers et al. (2011) *PLoS ONE*. 6(9): e24308, 1-11; McBride et al. (2011) 19(12): 2152-2162). In such embodiments, the anti-sense RNA need not be complementary to the entire sequence of the gene to be repressed, but can be substantially identical to at least a portion of the gene to be repressed. Generally, higher homology can be used to compensate for the use of a shorter sequence. In certain embodiments, a sequence of at least 30 nucleotides is used (e.g., at least 40, 50, 80, 100, 200, 500 nucleotides or more).

The methods disclosed herein treat diseases by either supplementing lost gene function or repressing gene aberrant expression of genes. Examples of diseases treated by the disclosed methods include Parkinson's Disease, Huntington's Disease, Alzheimer's disease, dementia, depression, alcoholism, substance dependence, autism spectrum disorders, post-traumatic stress disorder (PTSD), traumatic brain injury (TBI), chronic traumatic encephalopathy (CTE), CNS lupus, autoimmune diseases of the CNS, epilepsy, stroke, multiple sclerosis, amyotrophic lateral sclerosis, pain disorders, and neuromuscular diseases. Genetic diseases, in particular, can be amenable to treatment by the disclosed methods. Examples of such genetic diseases with CNS symptoms include Aicardi Syndrome, Alpers' Disease, Barth Syndrome (BTHS), Batten Disease, Colpocephaly, Fabry's Disease, Fahr's Syndrome, Galactosemia, Type 2 or 3 Gaucher Disease, Gerstmann-Straussler-Scheinker Disease, GM1 gangliosidosis, Leigh's Disease, Lesch-Nyhan Syndrome, Maple Syrup Urine Disease, Menkes Disease, Moyamoya Disease, Niemann-Pick Disease, Rett Syndrome, Urea Cycle Disorders, and Tay Sach's Disease, and Zellweger Syndrome. Many other diseases not listed or yet described may respond to treatment with the disclosed methods. Treatment of tumors also may be effective by the disclosed methods. Such tumors can be derived from neurons and glial cells. Furthermore, tumors of neuronal or glial cell origin can be malignant or benign. In certain embodiments, the tumors are growths of metastatic cells from other tissues. Metastases can spread from other tissues such as lung, bone, pancreas, colon, stomach, skin, and blood. In additional embodiments, the neurons treated by the methods are selected from the group consisting of dopaminergic neurons, cholinergic neurons, glutamatergic neurons GABAergic neurons and serotonergic neurons. In other embodiments, expression in specific cell types, such as particular types of neurons, astrocytes or glial cells, may be selected by appropriate use of gene expression control elements. Examples of control elements include the TH promoter should restrict expression to dopaminergic neurons, the glial fibrillary acidic protein (GFAP) promoter to glial cells.

Aspects of the disclosed methods comprise combination therapies. Such combination therapies include intranasal administration of the nanoparticles with a second therapeutic agent. Therapeutic agents can include any agent that is useful to treat a neurological or psychiatric disease. For example, a subject can administer the compacted plasmid DNA nanoparticles comprising a nucleic acid that encodes a polypeptide having GDNF activity (e.g., CK-PEG-GDNF) to treat Parkinson's Disease, while taking Levodopa. In combination therapies, the second therapeutic agent can be taken prior to, simultaneously with, or after intranasal administration of the compacted plasmid DNA nanoparticles.

4. Compositions

Aspects disclosed herein relate to compositions comprising nucleic acid nanoparticles. Such nanoparticles comprise essentially single molecules of nucleic acids, such as mRNA, anti-sense RNA, or plasmid DNA. The nanoparticles may comprise or express anti-sense moieties to reduce host mRNAs and/or proteins.

One such vector (pGDNF-1b) is shown in FIG. 1. The pGDNF-1b plasmid contains an origin of replication (R6K ori), an SV40 poly-A tail encoding sequence (SV40 pA), and the gene that confers Zeocin™ resistance (ZeoR) in bacteria containing the plasmid. In addition, the plasmid contains the hGDNF-1b gene sequence. The plasmid also contains a UbC promoter (UbC prom) to provide constitutive expression of the hGDNF nucleic acid sequence.

As shown in FIG. 1, plasmids within the scope of the disclosure can also contain additional sequences. For instance, plasmids can contain scaffold/matrix attachment region ("S/MAR" or "MAR") (FIG. 1; see also Fletcher A M, Kowalczyk T H, Padegimas L, Cooper M J, and Yurek D M. (2011) *Neuroscience*, 194:220-226.). Such regions can mediate structural organization of chromatin and have a role in gene expression.

Methods of making CK-PEG nanoparticles, such CK-PEG-GDNF nanoparticles, are disclosed in U.S. Pat. Nos. 8,017,577, 6,506,890, 6,281,005. 5,844,107, 5,877,302, 6,008,336, 6,077,835, 5,972,901, 6,200,801, and 5,972,900, the entirety of all of which are incorporated by reference. It should be noted that CK-PEG-GDNF nanoparticles can comprise polylysine and derivatives of polylysine. In certain embodiments, the polylysine comprises 15-60 lysine residues. In particular embodiments, the polylysine comprises lysine residues in the ranges of 15-30, 30-45, or 45-60 residues. In particular embodiments, derivatives of polylysine in CK-PEG-GDNF nanoparticles are CK15, CK30, CK45, which have an additional cysteine residue attached to polylysine polymers of length 15, 30, and 45 residues, respectively. Other amino acids can be readily attached to polylysine without departing from the spirit of the invention.

Aspects of the compositions disclosed herein include CK-PEG-GDNF nanoparticles comprising polylysine peptides that include alternative modified or alternative amino acids. For example, the individual lysine residues in the polylysine can be modified by acetylation to acetyllysine, methylation to methyllysine, ubiquitination, sumoylation, neddylation, biotinylation, pupylation, and carboxylation.

In addition, methods of making CK-PEG-GDNF nanoparticles having cysteine-polylysine peptides conjugated to polyethylene glycol are known in the art (see, e.g., Liu et al. (2003) *J. Biol. Chem.* 278(35): 32578-32586). PEGylation of polypeptides, including polylysine, for the generation of nanoparticles disclosed herein involve mixing a purified polypeptide that terminates with a single cysteine (CK) and methoxy-PEG10K-maleimide (id.). The maleimide and cysteine residues form a PEGylated peptide.

In certain embodiments, the CK-PEG-GDNF nanoparticles are made using between 0.1 mg/ml and 10 mg/ml of DNA added to between 1.0 mg/ml and 20 mg/ml polyether-conjugated polypeptide. In particular embodiments, the DNA concentration in the final mixture is between 0.05 mg/ml and 2.0 mg/ml. In more particular embodiments, the ratio of positive to negative charges is around 2:1 (see U.S. Pat. No. 8,017,577; see also Fink T L, Klepcyk P J, Oette S M, Gedeon C R, Hyatt S L, Kowalczyk T H, Moen R C, and Cooper, M J. (2006) *Gene Ther*, 13:1048-1051; Ziady A G, Gedeon C R, Miller T, Quan W, Payne J M, Hyatt S L, Fink T L, Muhammad O, Oette S, Kowalczyk T, Pasumarthy M K, Moen R C, Cooper M J, and Davis P B: (2003) *Mol Ther*, 8:936-947).

In additional embodiments, bifunctional PEGylation is performed on the polypeptide. Such bifunctional PEGylation can be performed using PEG-[OPSS]$_2$ (ortho-pyridyl disulfide) (see, e.g., Sun W and Ziady A G. (2009) *Methods Mol Biol.* 544:525-546). Such bifunctional PEGylation allows for targeting agents to be conjugated to the PEGylated polypeptide. Targeting agents include ligands, peptidomimetic compounds, receptor agonists, receptor antagonists, and small molecule compounds. An example of a targeting agent is dopamine attached to the bifunctional PEG to direct the nanoparticles to dopamine receptors.

Aspects of the compositions disclosed herein comprise nanoparticles having a size of less than or equal to 500 nanometers. In still other embodiments, the nanoparticles are less than or equal to 100 nanometers. In particular embodiments, the nanoparticles are less than or equal to 50 nanometers. In more particular embodiments, the nanoparticles are less than or equal to 25 nanometers. The minimum cross-sectional diameter of commonly used nanoparticles, such as the rod-like forms (FIG. 10) used in these Examples, is about 9-11 nm (see Fink T L, Klepcyk P J, Oette S M, Gedeon C R, Hyatt S L, Kowalczyk T H, Moen R C, and Cooper, M J. (2006) *Gene Ther*, 13:1048-1051).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

EXAMPLES

Figure 2:
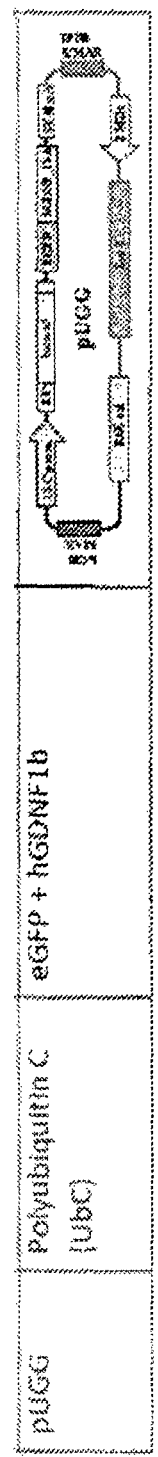
FIG. 2 shows the structure of the pUGG plasmid used in experiments on rats.
Figure 3A:
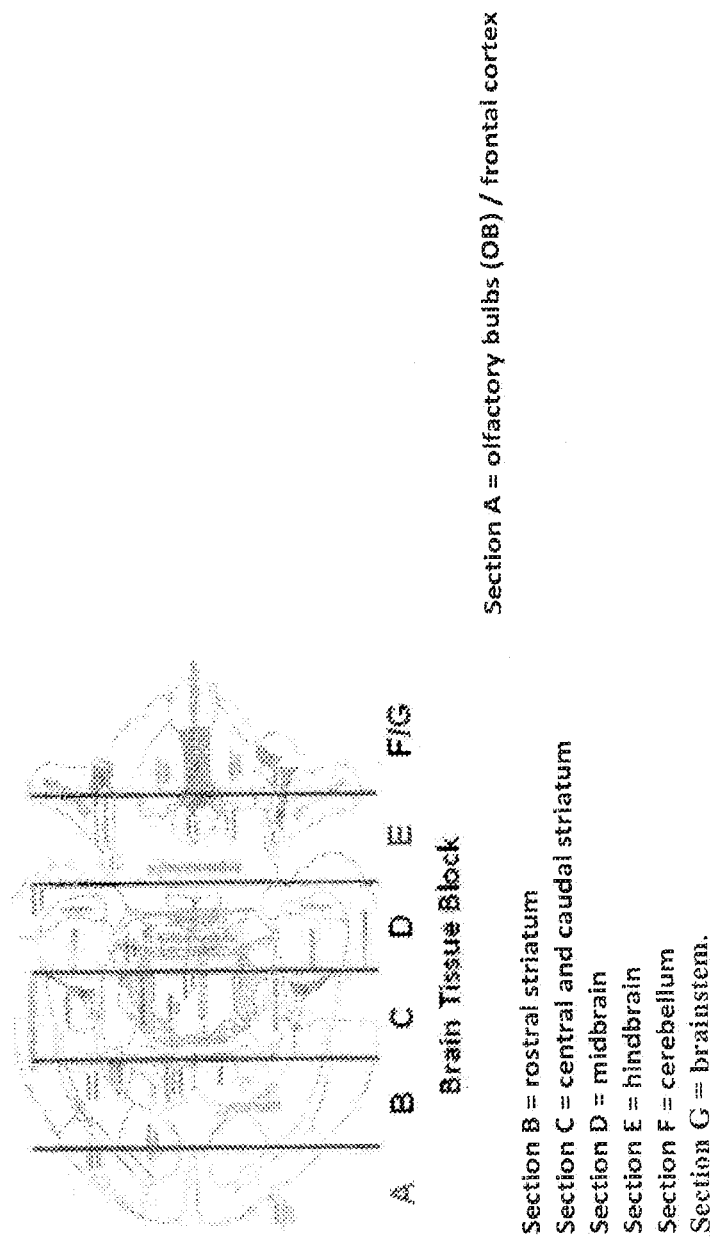
FIG. 3A shows a diagram of the tissue blocks prepared from rats that received intranasal administration of pUGG 7 days before sacrifice. The brain blocks, designated "A" through "F/G", were prepared by razor cuts along the coronal plane using a plexiglass rat brain matrix. Cuts were made at the locations indicated by the black lines. The brain regions within in each block are listed below the figure.
Figure 3B:
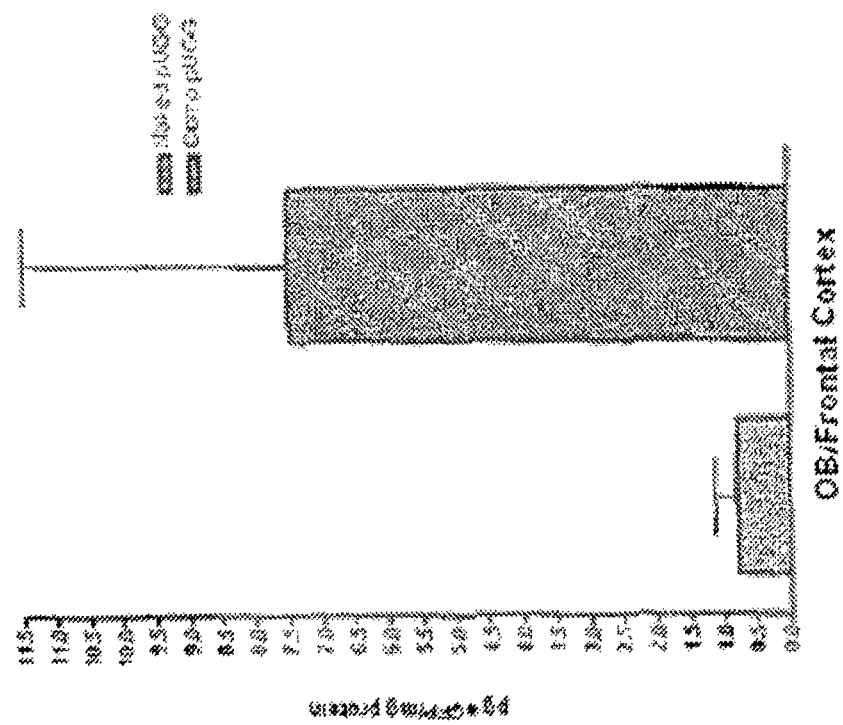
FIG. 3B shows a graph of GFP expression in section A, corresponding to the olfactory bulbs (OB) and frontal cortex, of rats 7 days after intranasal administration of 88 ug of compacted pUGG nanoparticles (n=4 rats) vs. naked pUGG (n=4 rats). GFP expression was determined by ELISA.

A non-limiting representative nanoparticles according to the disclosure were prepared and used.
Materials and Instrumentation CK$_{30}$PEG10k nanoparticles comprised of essentially single molecules of plasmid DNA having the human GDNF gene were obtained from Copernicus Therapeutics, Inc. (Cleveland, Ohio) (see FIGS. 1, 2, and 10). Copernicus Therapeutics provided two expression plasmids for this research: pUGG (hGDNF variant 1b linked to enhanced green fluorescent protein (eGFP) under transcriptional control by the polyubiquitin C promoter) and pGDNF-1b (hGDNF-1b under the same promoter) (id.). pUGG produces a GFP-GDNF fusion protein, which enabled detection of transfection and expression in brain. pGDNF-1b, which lacks the GFP sequence, was used in the 6-OHDA neuroprotection studies. Sprague-Dawley rats used in the experiment were obtained from Taconic Farms, Germantown, N.Y.
Analysis of CK$_{30}$PEG10K Nanoparticles Electron micrograph analysis of PEGylated polylysine DNA nanoparticles showed that the nanoparticles had a rod-like shape if formed using an acetate counterion for lysine (FIG. 10; Scale bar=200 nm) see Fink T L, Klepcyk P J, Oette S M, Gedeon C R, Hyatt S L, Kowalczyk T H, Moen R C, and Cooper, M J. (2006) *Gene Ther*, 13:1048-1051.
Testing Transfection and Expression of Plasmid Nanoparticles in Rat Brains Rats were given either pUGG nanoparticles or the naked plasmid intranasally (88 μg DNA; 20 μl in 2.5 μl increments alternating sides) using a 10 microliter Hamilton syringe fitted with a 5 mm length of polyethylene tubing. After 7 days, animals were sacrificed and brains were cut into coronal sections. Expression in each of the brain sections was determined by GFP-ELISA. The capture antibody was mouse anti-GFP antibody (Sigma G6539, 1:4000). eGFP standards and brain homogenates were added, and the plates were incubated for 2 hours at room temperature. Detection of eGFP was performed using a rabbit anti-GFP antibody (Abcam 290, 1:4,000) and an anti-rabbit secondary antibody conjugated to HRP (GE NA0340, 1:4,000). SureBlue TMB substrate (KPL #52-00-01) was added for color development. Optical densities were read on a BioTek ELx800 plate reader with Gen5 software. Seven days after intranasal administration, GFP was detected all along the rostral-caudal axis of the brain in rats given pUGG nanoparticles, with the highest levels in the frontal cortex and olfactory bulbs, which lie just behind the nasal cavity (FIGS. 3A and 3B). This result shows that pUGG nanoparticles successfully transfect cells in the brain after intranasal delivery, and this transfection causes expression of the encoded protein.

Figure 4:
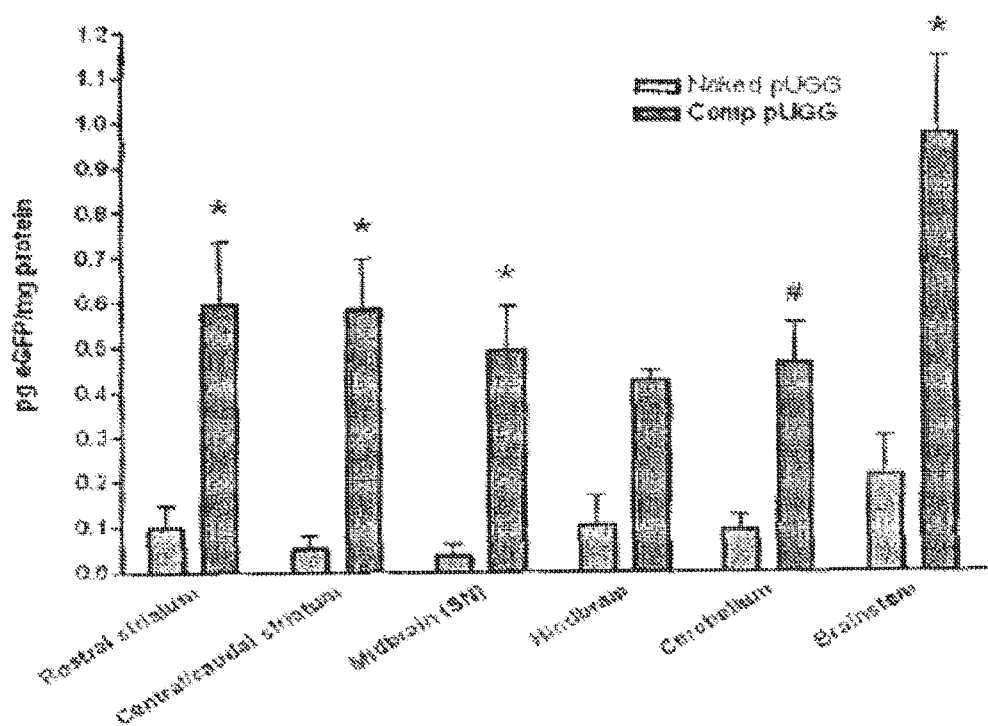
FIG. 4 shows GFP-ELISA results for sections B through F/G 7 days after intranasal administration (88 ug). 2-way ANOVA indicates a significant effect by treatment ($p<0.0001$) and by section ($p<0.0056$). Bonferroni post-tests indicate significant differences between compacted pUGG nanoparticles and naked pUGG (*$p<0.01$, #$p<0.05$).

In brain areas caudal to the frontal cortex, GFP levels were lower in general, but they remained significantly higher in rats given compacted pUGG nanoparticles than in those given the naked plasmid (FIG. 4). Importantly, GFP levels were significantly elevated in both the striatum and midbrain of rats given pUGG nanoparticles. These are the brain areas where the protein must be expressed for treatment of Parkinson's disease.

Studies of Effectiveness of pGDNF Nanoparticles in a Parkinson's Disease Model

Studies of Parkinson's Disease were performed in the rat 6-OHDA model. Rats were given either pGDNF-1b nanoparticles nanoparticles (NP), or the naked plasmid, (88 µg DNA; 20 µl in 2.5 µl increments alternating sides; n=7-8/group) or phosphate-buffered saline intranasally. Seven days later, when GDNF is being expressed, the rats were anesthetized and 6-0HDA (4 µl of 2 mg/ml; total dose 8 µg) was surgically injected into the left medial forebrain bundle. The injection was made at the following stereotaxic coordinates: −1.2 mm lateral, +0.44 mm anterior to the lambdoid suture and −8.3 mm ventral to the surface of the skull.

Figure 5:
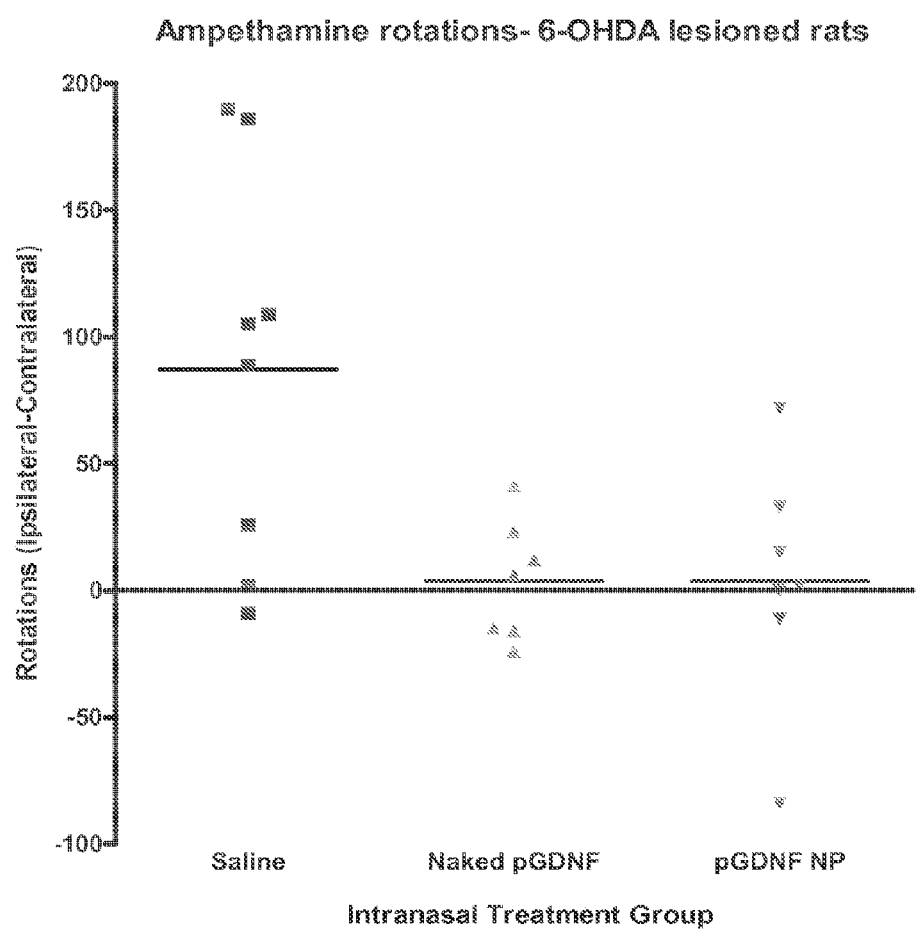
FIG. 5 shows ipsilateral rotation in 6-hydroxydopmaine (6-OHDA)-lesioned rats during the 30 min period after a dose of amphetamine. Rats were given an intranasal dose of saline, naked pGDNF-1b, or compacted pGDNF-1b nanoparticles (NP) one week before receiving a unilateral injection of 6-OHDA (4 μL of 2 mg/mL; total dose 8 μg) into the left median forebrain bundle. Three to four weeks later, lesioned rats were given a 5 mg/kg dose of d-amphetamine. pGDNF-1b (naked or NPs) significantly reduced ipsilateral rotations compared to saline controls. One-way ANOVA indicated a significant difference between groups ($p=0.01$); Dunnett's post-test showed significance for pGDNF NPs vs. saline (*$p<0.05$) and naked pGDNF vs. saline (*$p<0.05$).

Desipramine (15 mg/kg, i.p.) was given 30 min prior to surgery to spare norepinephrine neurons from the neurotoxin. This procedure generated a unilateral lesion of the substantia nigra (SN) dopamine neurons. The animals recovered for an additional 3-4 weeks and then were behaviorally assessed using an amphetamine challenge. Amphetamine (5 mg/kg, i.p.) causes rotational behavior in rats with a unilaterai6-0HDA lesion due to the imbalance between dopamine being released on the lesioned versus the unlesioned side. Rats with severe lesions rotated ipsilateral to the lesion (counter-clockwise), with rotation frequency generally correlating with lesion severity. FIG. 5 shows net ipsilateral rotations in rats during a 30 min interval after amphetamine was given. There was a trend for rats given intranasal saline to show more rotations (and thus a greater lesion severity). This suggests that dopamine neurons were protected on the lesioned side in rats given intranasal pGDNF-1b.

Figure 6:
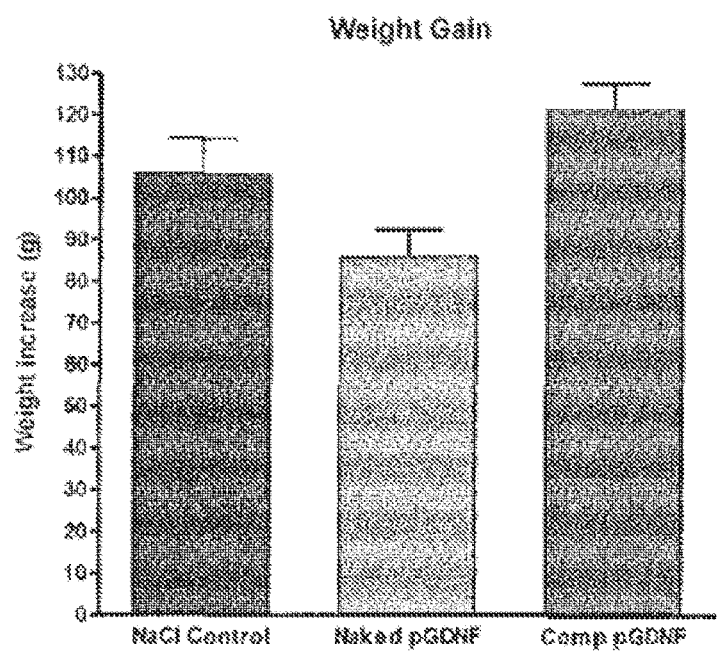
FIG. 6 shows body weight gain differences in rats 3-4 weeks after a 6-0HDA lesion. Experimental conditions were identical to FIG. 5.

Weight gain, another possible index of neuroprotection (i.e. reduced lesion severity), was significantly greater in the pGDNF-1b NP treatment group compared to saline controls and the naked pGDNF-1b group in the 3-4 weeks between the 6-OHDA lesion and sacrifice (FIG. 6). One-way ANOVA indicated significance by treatment (p=0.0035); Tukey's post-test indicated significant differences between saline and pGDNF-1b NP (p<0.05) as well as between naked pGDNF-1b and pGDNF-1b NP. (id.).

Figure 7:
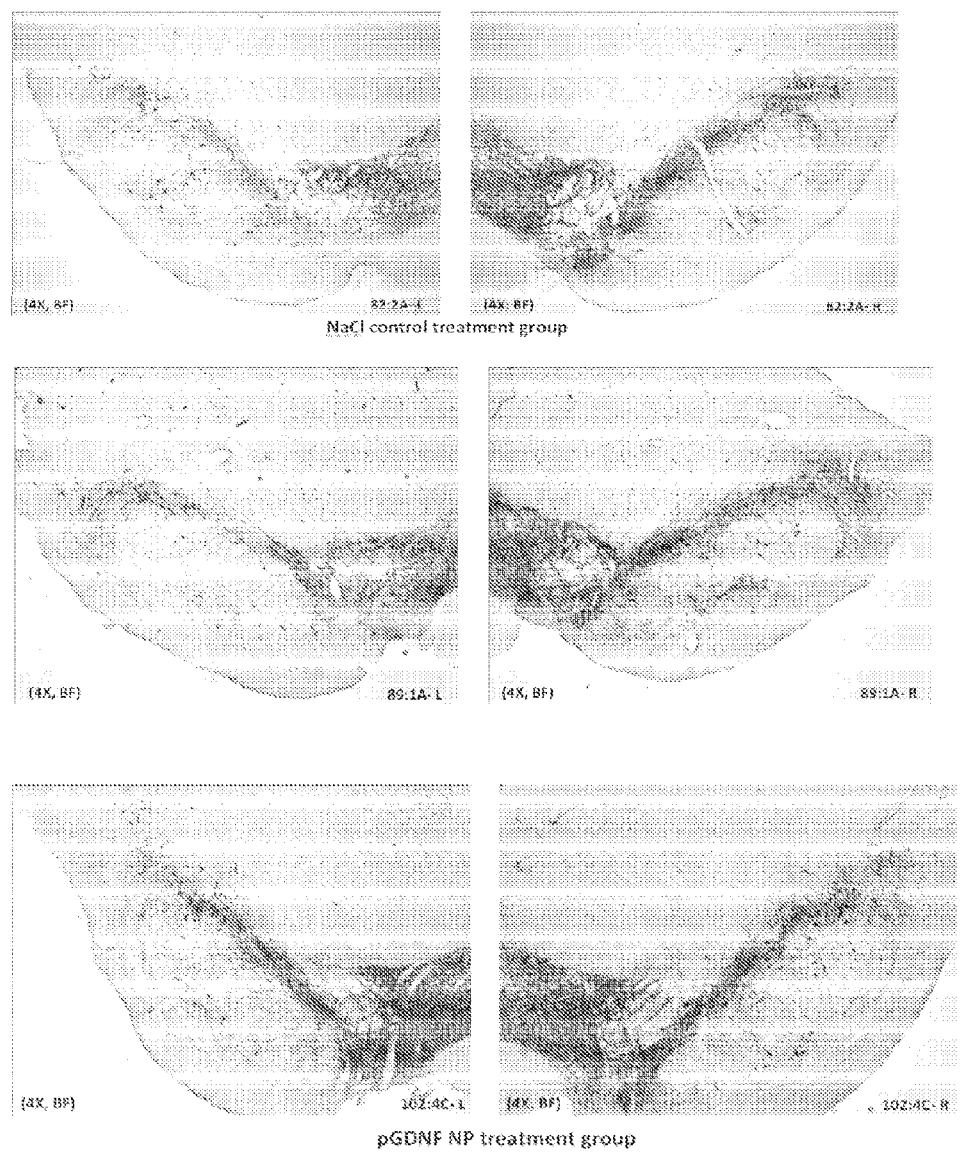
FIG. 7 shows representative brain sections of the lesioned (left) and unlesioned (right) substantia nigra (SN) of rats given intranasal (IN) saline (top) or 88 ug of naked pGDNF-1b (middle), or pGDNF-1b NPs (bottom) 7 days before 6-OHDA. Rats were sacrificed 3 to 4 weeks after the 6-OHDA injection. The brown stain indicates tyrosine hydroxylase (TH) immunohistochemical staining of dopamine neurons.

Evidence of Effectiveness of pGDNF Nanoparticles in Brain Sections of Treated Rats After completion of the amphetamine challenge, rats were deeply anesthetized and sacrificed by transcardial perfusion with 4% paraformaldehyde. Sections from the substantia nigra (SN) of each rat were collected for tyrosine hydroxylase (TH) immunohistochemistry (IHC). TH is a marker for dopamine neurons. Representative SN sections are shown in FIG. 7. BIOQUANT image analysis software was used to measure TH immunostaining density in both the lesioned and unlesioned SN of each rat, with the percentage subtracted from 100 to calculate the % lesion. For each animal, this value represents the mean staining from 6 sections along the rostral to caudal axis of the SN.

Figure 8:
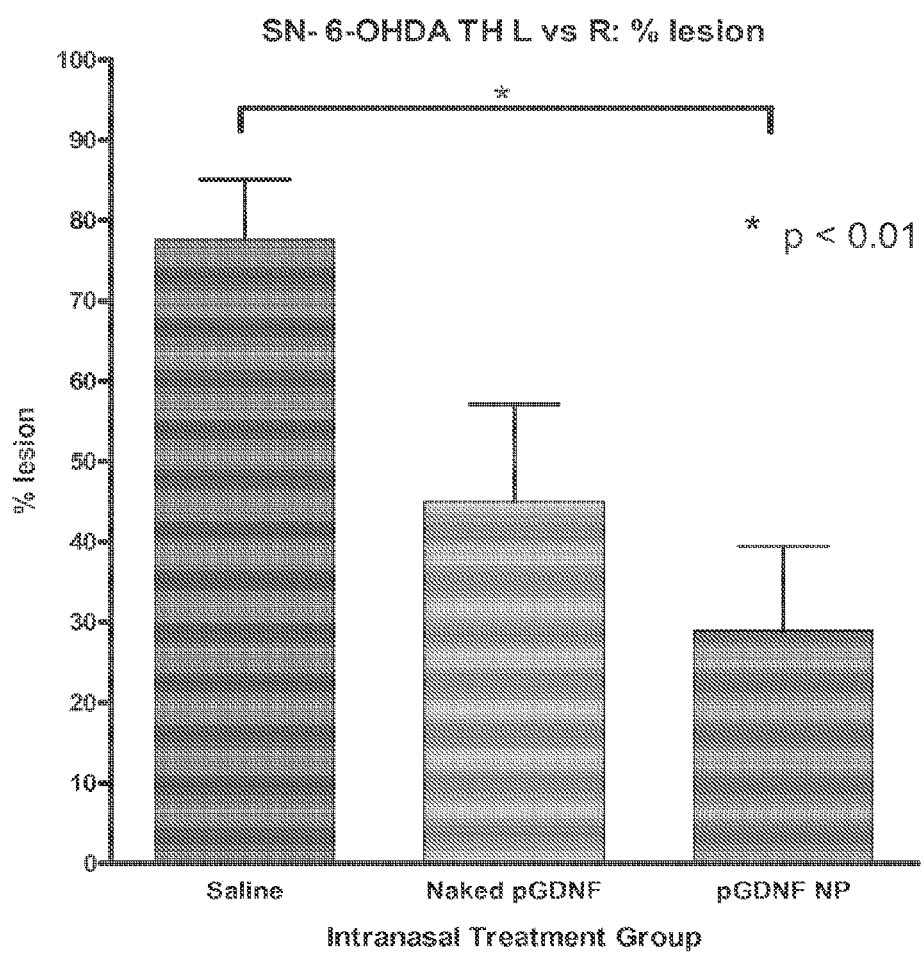
FIG. 8 shows percent lesion in the 6-OHDA-lesioned substantia nigra (SN) of rats given intranasal naked or compacted pGDNF-1b and controls given intranasal saline. Experimental conditions were identical to FIGS. 5, 6, 7. Lesion severity (% lesion) was assessed by comparing tyrosine hydroxylase (TH) staining density on the left (lesioned) vs. right (intact) side from 7-8 rats per treatment group. One-way ANOVA indicated a significant effect due to treatment ($p=0.0081$); Tukey's post-test showed a significant difference between pGDNF-1b NP vs. saline (*$p<0.01$).

Results showed that rats given compacted pGDNF-1b intranasally one week prior to the lesion had significantly greater TH staining density in the SN than those given naked pGDNF-1b or intranasal saline. These results are consistent with a neuroprotective effect of intranasal pGDNF-1b nanoparticles in the 6-OHDA model (FIGS. 8 and 9).

TH staining intensity and dopamine cell counts were higher in the 6-OHDA-lesioned SN of rats given IN pGDNF-1b than in controls given IN saline. Lesion severity was assessed by comparing TH staining density on the left (lesioned) vs. right (intact) side (FIG. 8). Rats given IN saline had an average lesion of 77.7% whereas rats given IN naked pGDNF-1b and pGDNF-1b NPs had lesions of only 45.0% and 28.9%, respectively. One-way ANOVA indicated a significant effect from treatment (p=0.0081); Tukey's post-test showed a significant difference between pGDNF-1b NP vs. saline (*p<0.01) (id.).

Figure 9:
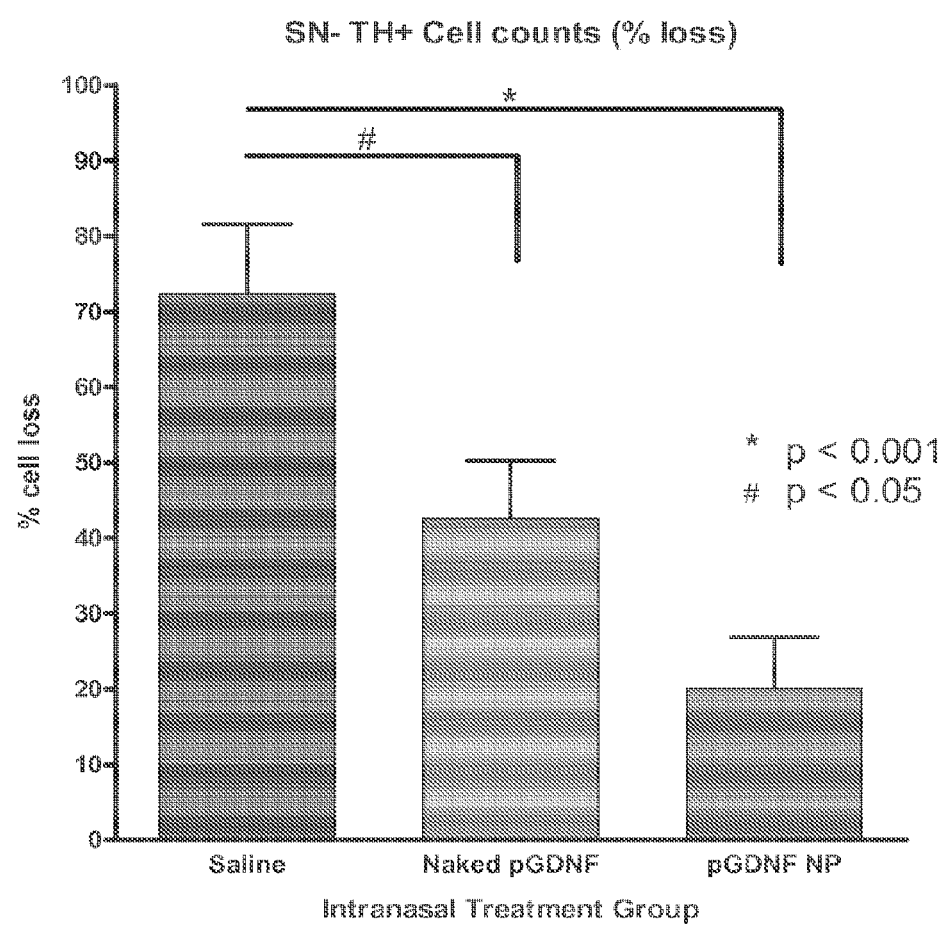
FIG. 9 shows percent cell loss in the 6-OHDA-lesioned substantia nigra (SN) of rats given intranasal naked or compacted pGDNF-1b and controls given intranasal saline. Experimental conditions were identical to FIGS. 5, 6, 7, 8. Lesion severity (% cell loss) was assessed by comparing the number of TH positive (dopamine) neurons in the lesioned vs. intact substantia nigra from 7-8 rats per treatment group. One-way ANOVA indicated a significant effect due to treatment ($p=0.0008$); Tukey's post-test showed significant differences for pGDNF NP vs. saline (*$p<0.001$) and for naked pGDNF-1b vs. saline (#$p<0.05$).

Lesion severity was also assessed by comparing the number of TH positive (i.e. dopamine) neurons in the lesioned vs. intact SN (FIG. 9). The % dopamine cell loss was significantly less in the lesioned SN of rats given intranasal pGDNF-1b. The protective effect was greater in rats that received intranasal pGDNF-1b nanoparticles than the naked plasmid. One-way ANOVA indicated a significant effect from treatment (p=0.0008); Tukey's post-test showed significant differences for pGDNF-1b NP vs. saline (*p<0.001) and for naked pGDNF-1b vs. saline (#p<0.05) (id.).

The invention claimed is:

1. A method for delivering and expressing a nucleic acid in the brain, the method comprising intranasal administration of nucleic acid nanoparticles, wherein the administered nanoparticles comprise a ratio of about one molecule of nucleic acid per one nanoparticle, and wherein the nucleic acid comprises a nucleic acid sequence of SEQ ID NO: 1.

2. The method of claim 1, wherein the nucleic acid encodes a therapeutic protein.

3. The method of claim 1, wherein the nucleic acid nanoparticle further comprises a polycation.

4. The method of claim 3, wherein the polycation is a polylysine.

5. The method of claim 1, wherein the nucleic acid nanoparticles comprise plasmid DNA.

6. The method of claim 1, wherein the nucleic acid encodes a polypeptide having GDNF activity.

7. The method of claim 6, wherein the polypeptide has an amino acid sequence of SEQ ID NO: 2.

8. The method of claim 2, wherein the nucleic acid nanoparticles express a product that is controlled by a tissue-specific promoter.

9. The method of claim 8, wherein the promoter is TH promoter or the glial fibrillary acidic protein (GFAP) promoter.

* * * * *

SEQUENCE LISTING

<160> NUMBER OF SEQ ID NOS: 2

<210> SEQ ID NO 1
<211> LENGTH: 4064
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
ttaattaaaa ttatctctaa ggcatgtgaa ctggctgtct tggttttcat ctgtacttca      60
tctgctacct ctgtgacctg aaacatattt ataattccat taagctgtgc atatgataga     120
tttatcatat gtattttcct taaaggattt ttgtaagaac taattgaatt gatacctgta     180
```

```
aagtctttat cacactaccc aataaataat aaatctcttt gttcagctct ctgtttctat    240
aaatatgtac cagttttatt gttttagtg gtagtgattt tattctcttt ctatatatat    300
acacacacat gtgtgcattc ataaatatat acaattttta tgaataaaaa attattagca    360
atcaatattg aaaaccactg attttgtttt atgtgagcaa acagcagatt aaaaggaatt    420
cctgcaggcc tccgcgccgg gttttggcgc ctcccgcggg cgccccctc ctcacggcga    480 gcgctgccac gtcagacgaa gggcgcagcg agcgtcctga tccttccgcc cggacgctca    540
ggacagcggc ccgctgctca taagactcgg ccttagaacc ccagtatcag cagaaggaca    600
ttttaggacg ggacttgggt gactctaggg cactggtttt ctttccagag agcggaacag    660
gcgaggaaaa gtagtcccct tcggcgatt ctgcggaggg atctccgtgg ggcggtgaac    720
gccgatgatt atataaggac gcgccgggtg tggcacagct agttccgtcg cagccgggat    780
ttgggtcgcg gttcttgttt gtggatcgct gtgatcgtca cttggtgagt agcgggctgc    840
tgggctggcc ggggctttcg tggccgccgg gccgctcggt gggacggaag cgtgtggaga    900
gaccgccaag ggctgtagtc tgggtccgcg agcaaggttg ccctgaactg ggggttgggg    960
ggagcgcagc aaaatggcgg ctgttcccga gtcttgaatg gaagacgctt gtgaggcggg   1020
ctgtgaggtc gttgaaacaa ggtgggggc atggtgggcg gcaagaaccc aaggtcttga   1080
ggccttcgct aatgcgggaa agctcttatt cgggtgagat gggctgtggc accatctggg   1140
gaccctgacg tgaagtttgt cactgactgg agaactcggt tgtcgtctg ttgcgggggc   1200 ggcagttatg gcggtgccgt tgggcagtgc acccgtacct ttgggagcgc gcgccctcgt   1260
cgtgtcgtga cgtcacccgt tctgttggct tataatgcag ggtggggcca cctgccggta   1320
ggtgtgcggt aggcttttct ccgtcgcagg acgcagggtt cgggcctagg gtaggctctc   1380
ctgaatcgac aggcgccgga cctctggtga ggggagggat aagtgaggcg tcagtttctt   1440
tggtcggttt tatgtaccta tcttcttaag tagctgaagc tccggttttg aactatgcgc   1500
tcggggttgg cgagtgtgtt ttgtgaagtt tttaggcac cttttgaaat gtaatcattt   1560
gggtcaatat gtaattttca gtgttagact agtaaattgt ccgctaaatt ctggccgttt   1620
ttggcttttt tgttagacga gctagcccac catgaagtta tgggatgtcg tggctgtctg   1680
cctggtgctg ctccacaccg cgtccgcctt cccgctgccc gccggcaaga ggcctcccga   1740
ggcgcccgcc gaagaccgct ccctcggccg ccgccgcgcg cccttcgcgc tgagcagtga   1800
ctcaaatatg ccagaggatt atcctgatca gttcgatgat gtcatggatt ttattcaagc   1860
caccattaaa agactgaaaa ggtcaccaga taaacaaatg gcagtgcttc ctagaagaga   1920
gcggaatcgg caggctgcag ctgccaaccc agagaattcc agaggaaaag gtcggagagg   1980
ccagagggga aaaaccgggg gttgtgtctt aactgcaata catttaaatg tcactgactt   2040
gggtctgggc tatgaaacca aggaggaact gattttagg tactgcagcg gctcttgcga   2100
tgcagctgag acaacgtacg acaaaatatt gaaaaactta ccagaaaata gaaggctggt   2160
gagtgacaaa gtagggcagg catgttgcag acccatcgcc tttgatgatg acctgtcgtt   2220
tttagatgat aacctggttt accatattct aagaaagcat tccgctaaaa ggtgtggatg   2280
tatctgataa tctagactag ctggccagac atgataagat acattgatga gtttggacaa   2340
accacaacta gaatgcagtg aaaaaaatgc ttatttgtg aaatttgtga tgctattgct   2400
ttatttgtaa ccattataag ctgcaataaa caagttaaca acaacaattg cattcatttt   2460
atgtttcagg ttcaggggga ggtgtgggag gttttttaaa gcaagtaaaa cctctacaaa   2520
tgtggtatgg aattcagtca atatgttcac cccaaaaaag ctgtttgtta acttgccaac   2580
```

```
ctcattctaa aatgtatata gaagcccaaa agacaataac aaaaatattc ttgtagaaca    2640
aaatgggaaa gaatgttcca ctaaatatca agatttagag caaagcatga gatgtgtggg    2700
gatagacagt gaggctgata aaatagagta gagctcagaa acagacccat tgatatatgt    2760
aagtgaccta tgaaaaaaat atggcatttt acaatgggaa aatgatgatc ttttctttt     2820 ttagaaaaac agggaaatat atttatatgt aaaaataaa agggaaccca tatgtcatac     2880
catacacaca aaaaaattcc agtgaattat aagtctaaat ggagaaggca aaactttaaa    2940
tcttttagaa aataatatag aagcatgcca tcaagacttc agtgtagaga aaaatttctt    3000
atgactcaaa gtcctaacca caagaaaag attgttaatt agattgcatg aatattaaga    3060 cttatttta aaattaaaaa accattaaga aaagtcaggc catagaatga cagaaaatat    3120
ttgcaacacc ccagtaaaga gaattgtaat atgcagatta taaaaagaag tcttacaaat    3180
cagtaaaaaa taaaactaga caaaaatttg aacagatgaa agagaaactc taaataatca    3240
ttacacatga gaaactcaat ctcagaaatc agagaactat cattgcatat acactaaatt    3300
agagaaatat taaaaggcta agtaacatct gtggcttaat taaaacagta gttgacaatt    3360
aaacattggc atagtatatc tgcatagtat aatacaactc actataggag ggccatcatg    3420
gccaagttga ccagtgctgt cccagtgctc acagccaggg atgtggctgg agctgttgag    3480
ttctggactg acaggttggg gttctccaga gattttgtgg aggatgactt tgcaggtgtg    3540
gtcagagatg atgtcaccct gttcatctca gcagtccagg accaggtggt gcctgacaac    3600
accctggctt gggtgtgggt gagaggactg gatgagctgt atgctgagtg gagtgaggtg    3660
gtctccacca acttcaggga tgccagtggc cctgccatga cagagattgg agagcagccc    3720
tgggggagag agtttgccct gagagaccca gcaggcaact gtgtgcactt tgtggcagag    3780
gagcaggact gaggataacc taggaaacct taaaaccttt aaaagcctta tatattcttt    3840
tttttcttat aaaacttaaa accttagagg ctatttaagt tgctgattta tattaatttt    3900
attgttcaaa catgagagct tagtacatga aacatgagag cttagtacat tagccatgag    3960
agcttagtac attagccatg agggttagt tcattaaaca tgagagctta gtacattaaa    4020
catgagagct tagtacatac tatcaacagg ttgaactgct gatc                    4064
```

<210> SEQ ID NO 2
<211> LENGTH: 211
<212> TYPE: PRT
<213> ORGANISM: Homo sapiens

<400> SEQUENCE: 2

```
Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
                20                  25                  30

Ala Glu Asp Arg Ser Leu Gly Arg Arg Arg Ala Pro Phe Ala Leu Ser
            35                  40                  45

Ser Asp Ser Asn Met Pro Glu Asp Tyr Pro Asp Gln Phe Asp Asp Val
        50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110
```

```
Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
            165                 170                 175

Ala Cys Cys Arg Pro Ile Ala Phe Asp Asp Asp Leu Ser Phe Leu Asp
            180                 185                 190

Asp Asn Leu Val Tyr His Ile Leu Arg Lys His Ser Ala Lys Arg Cys
        195                 200                 205

Gly Cys Ile
    210
```